(12) United States Patent
Hashimoto et al.

(10) Patent No.: US 11,471,632 B2
(45) Date of Patent: Oct. 18, 2022

(54) MASK FITTING LEVEL DETERMINATION DEVICE

(71) Applicant: YAMAMOTO KOGAKU CO., LTD., Higashiosaka (JP)

(72) Inventors: Hiroki Hashimoto, Higashiosaka (JP); Kenichi Sakamoto, Higashiosaka (JP)

(73) Assignee: YAMAMOTO KOGAKU CO., LTD., Osaka (JP)

( * ) Notice: Subject to any disclaimer, the term of this patent is extended or adjusted under 35 U.S.C. 154(b) by 451 days.

(21) Appl. No.: 16/599,713

(22) Filed: Oct. 11, 2019

(65) Prior Publication Data

US 2020/0114106 A1 Apr. 16, 2020

(30) Foreign Application Priority Data

Oct. 16, 2018 (JP) .............................. JP2018-194878

(51) Int. Cl.
*A61M 16/06* (2006.01)
*A61M 16/00* (2006.01)

(52) U.S. Cl.
CPC .... *A61M 16/0605* (2014.02); *A61M 16/0003* (2014.02); *A61M 16/024* (2017.08);
(Continued)

(58) Field of Classification Search
CPC ............ A61M 16/0003; A61M 16/024; A61M 2016/0027; A61M 2205/15;
(Continued)

(56) References Cited

U.S. PATENT DOCUMENTS

2005/0263155 A1* 12/2005 Gossweiler ............ A62B 9/006
128/206.16
2012/0318266 A1* 12/2012 Chou .................. A61M 16/024
128/204.23
(Continued)

FOREIGN PATENT DOCUMENTS

JP 57-79739 5/1982
JP 63502007 A 8/1988
(Continued)

OTHER PUBLICATIONS

International Search Report issued in PCT/JP2018/031473 dated Oct. 16, 2018.
(Continued)

*Primary Examiner* — Margaret M Luarca
(74) *Attorney, Agent, or Firm* — Heslin Rothenberg Farley & Mesiti P.C.

(57) ABSTRACT

Provided is a mask fitting level determination device that has a significantly simple component configuration, that can be driven by a battery, that can be reduced in size to a palm size, that is inexpensive, that is operated by a simple operation method, and that does not require proficiency for accurate measurement. The mask fitting level determination device includes: a mask inner pressure detection unit 2 that is inserted between a face surface F of a mask wearing person and a worn mask 1; and a circuit control unit that sets a predefined threshold value in accordance with strength of breathing of the mask wearing person and determines a fitting level on the basis of a reference pressure value and a mask inner pressure value measure by the mask inner pressure detection unit 2; and a display unit 3 that displays the fitting level determined by the circuit control unit to the mask wearing person.

15 Claims, 5 Drawing Sheets

(52) U.S. Cl.
CPC . *A61M 2016/0027* (2013.01); *A61M 2205/13* (2013.01); *A61M 2205/15* (2013.01)

(58) Field of Classification Search
CPC ........ A61M 2016/0015; G01M 3/3272; A62B 18/025; A62B 27/00; A62B 9/006
See application file for complete search history.

(56) References Cited

U.S. PATENT DOCUMENTS

| 2013/0263857 | A1* | 10/2013 | Ahmad | A61M 16/107 128/205.23 |
| 2016/0166859 | A1 | 6/2016 | Rachapudi et al. | |
| 2018/0008849 | A1* | 1/2018 | Baker | A62B 27/00 |

FOREIGN PATENT DOCUMENTS

| JP | 2014085218 | A | 5/2014 |
| WO | 2013151944 | A1 | 10/2013 |

OTHER PUBLICATIONS

U.S. Appl. No. 16/636,808, filed Feb. 5, 2020, titled Mask Adhesion Determination Device.

* cited by examiner

MASK FITTING LEVEL DETERMINATION DEVICE

CROSS REFERENCE TO RELATED APPLICATIONS

This application is a U.S. Patent Application filing which claims priority to Japanese Application No.: 2018-194878, filed on Oct. 16, 2018, which is hereby incorporated by reference herein in its entirety.

BACKGROUND OF THE INVENTION

Field of the Invention

The present invention relates to a mask fitting level determination device capable of determining a fitting level when a mask is worn for breathing or the like that particularly requires a fittingness when the mask is worn for use as a dustproof mask, a gas mask, or the like at a place where dust or poisonous gas is generated, such as in a plant or at a construction site.

Description of the Related Art

In the related art, an intra-facepiece (mask) environment measurement device capable of checking a degree of leakage of particles in real time and checking a relationship between the leakage of the particles and breathing of a wearing person is present as such a type of mask fitting level determination device (Japanese Patent No. 5564728).

Such an intra-mask environment measurement device includes an intra-mask particle counter, an extra-mask particle counter, a pressure sensor that measures a pressure inside the mask, a particle number comparison calculating unit, and an output unit, measures the number of particles using a particle counter of a laser light scattering scheme, and determines concentration of the number of particles.

However, the aforementioned intra-mask environment measurement device in the related art is a stationary device with a significantly complicated structure and has a problem that the device has a large shape and is significantly expensive.

Further, the aforementioned intra-mask environment measurement device in the related art uses a sampling tube to be inserted into the mask, which is likely to affect the fittingness of the mask. That is, it is necessary to insert two tubes for extracting the particles in the mask and the pressure in the mask, into the mask, and there is a problem that the tubes themselves may cause some problems in the fittingness.

The aforementioned intra-mask environment measurement device in the related art has problems that an operation method is not simple and that proficiency is required for accurate measurement.

The invention was thus made, and an object thereof is to provide a mask fitting level determination device with a significantly simple component configuration that can be driven by a battery, that can be reduced in size to a palm size, that is inexpensive, that is operated by a simple operation method, and that does not require proficiency for accurate measurement.

SUMMARY OF THE INVENTION

According to the present invention, there is provided a mask fitting level determination device including: a mask inner pressure detection unit 2 that is inserted between a face surface F of a wearing person and a worn mask 1; a circuit control unit that sets a prescribed threshold value in accordance with strength of breathing of the wearing person and determines a fitting level on the basis of a reference pressure value and a mask inner pressure value measured by the mask inner pressure detection unit 2; and a display unit 3 that displays the fitting level determined by the circuit control unit to the wearing person.

In the mask fitting level determination device according to the invention, the mask inner pressure detection unit 2 is an ultra-small pressure sensor of a piezoresistive type and is inserted between the face surface F of the wearing person and the worn mask 1 via a flexible substrate B.

In the mask fitting level determination device according to the invention, for measurement of the reference pressure value, the mask inner pressure detection unit 2 is taken out of the mask, and an atmospheric pressure at a location where the person wears the mask is measured again every several minutes.

In the mask fitting level determination device according to the invention, the prescribed threshold value is set on the basis of a difference in variation between a mask inner pressure value caused by strength of breathing performed a plurality of times by the mask wearing person before the fitting level is determined and the reference pressure value.

In the mask fitting level determination device according to the invention, the fitting level is determined on the basis of a difference in variation between a mask inner pressure value caused by strength of breathing performed a plurality of times by the mask wearing person when the fitting level is determined and the prescribed threshold value.

Since the mask fitting level determination device according to the invention is configured as described above, the mask fitting level determination device has a significantly simple component configuration, can be driven by a battery, can be reduced in size to a palm size, is inexpensive, is operated by a simple operation method, and does not require proficiency for accurate measurement.

DETAILED DESCRIPTION OF THE PREFERRED EMBODIMENT

Hereinafter, an embodiment for implementing a mask fitting level determination device according to the invention will be described in detail with reference to drawings.

Figure 1:
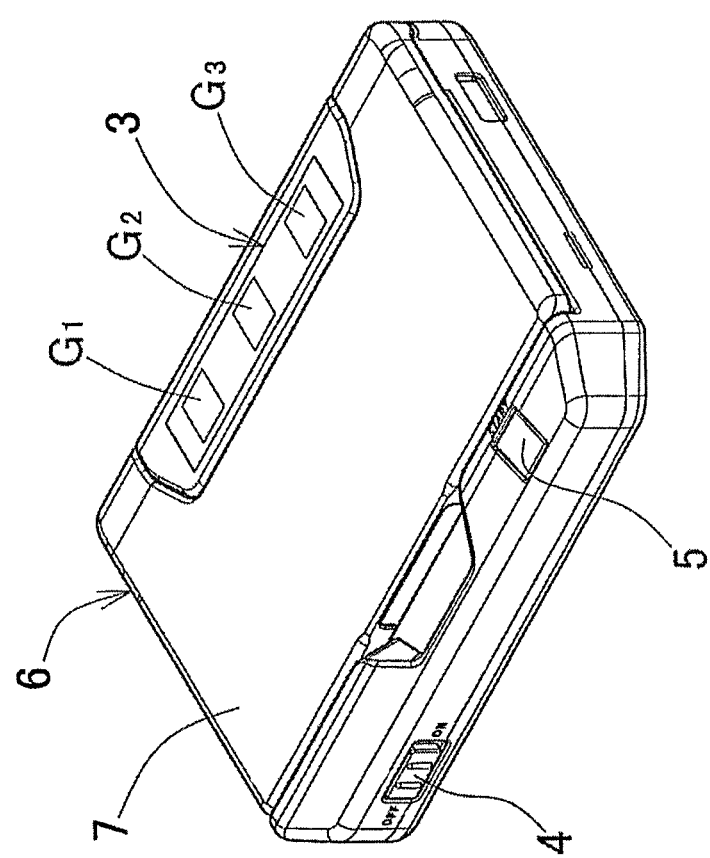
FIG. 1 is a perspective view illustrating an appearance of a mask fitting level determination device according to the invention.
Figure 2:
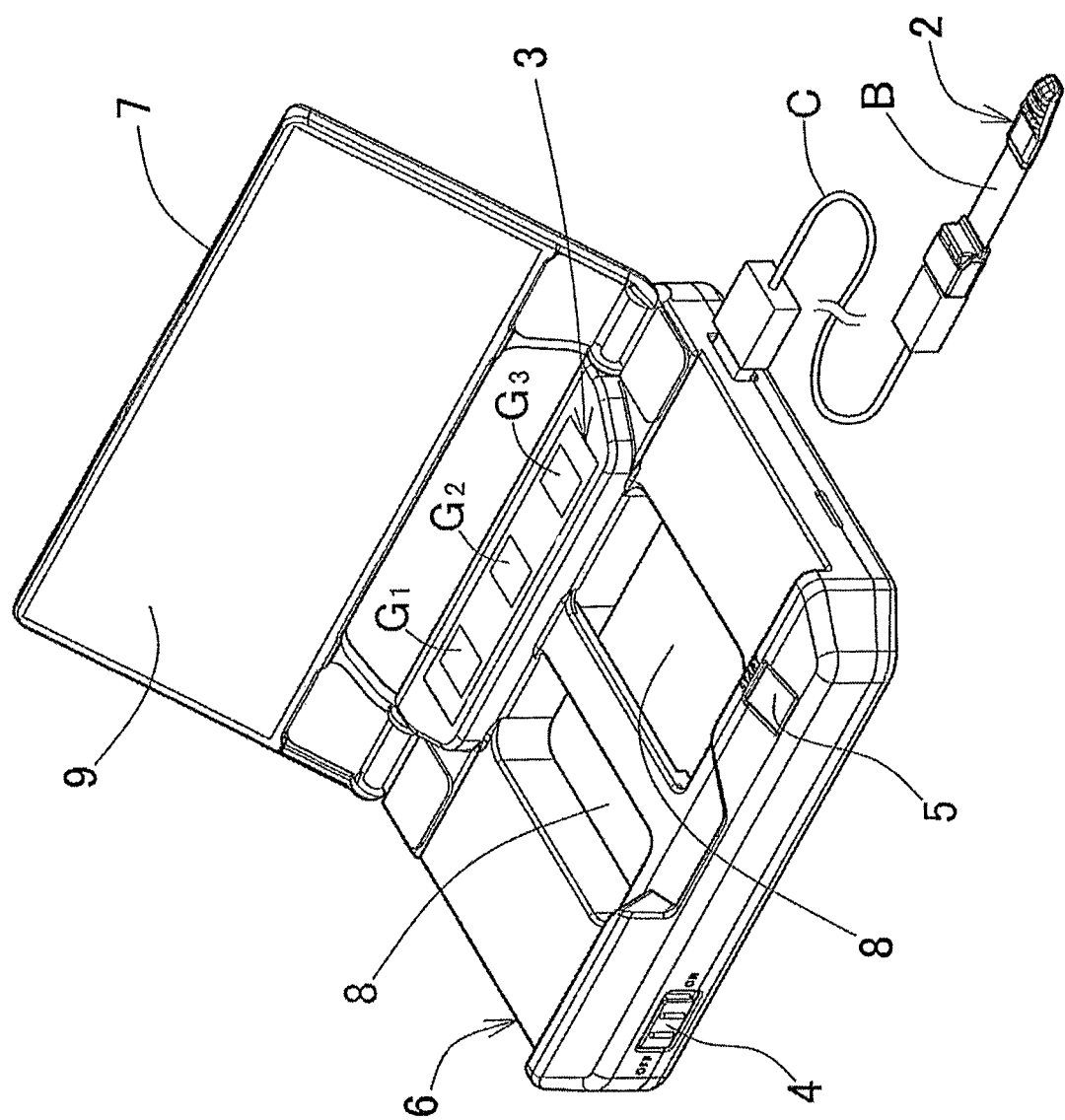
FIG. 2 is a perspective view illustrating a state in which an opening/closing lid of the mask fitting level determination device according to the invention illustrated in FIG. 1 is opened.
Figure 3:
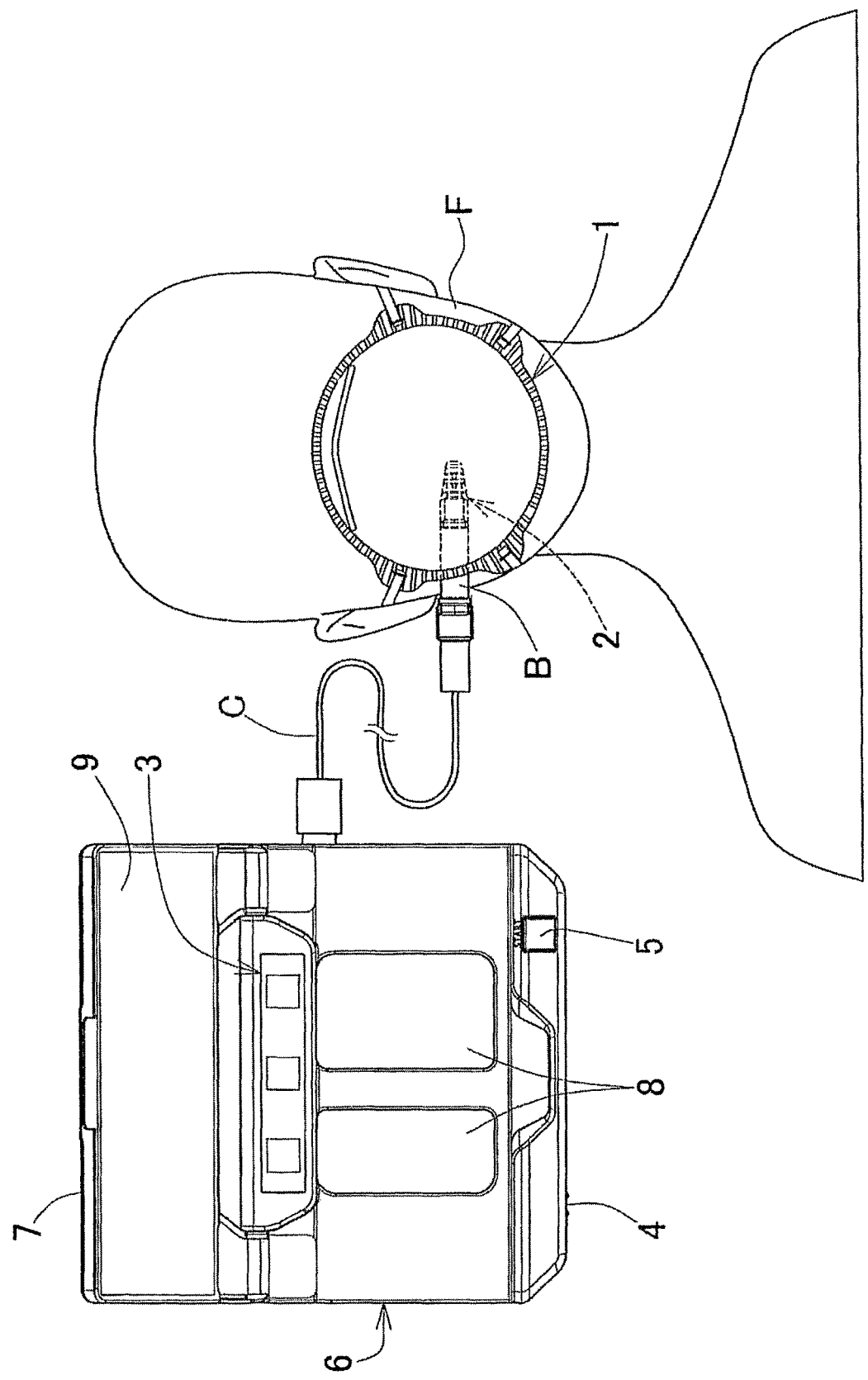
FIG. 3 is an explanatory diagram illustrating a state in which the mask fitting level determination device according to the invention is used.
Figure 4:
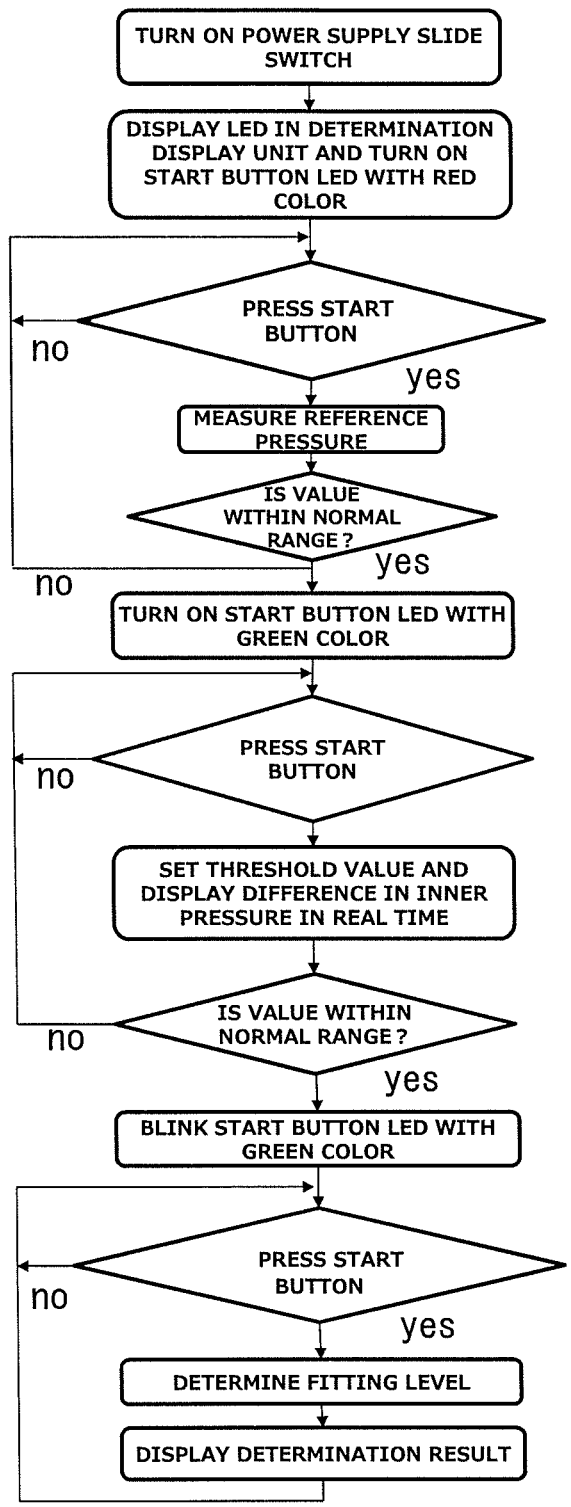
FIG. 4 is a flowchart illustrating a procedure for determining a fitting level using the mask fitting level determination device according to the invention.

The mask fitting level determination device according to the invention includes a mask inner pressure detection unit 2 that is inserted between a face surface F of a wearing person and a mask 1 worn such that a mouth and a nose are covered, a circuit control unit (not illustrated) that sets a prescribed threshold value in accordance with strength of breathing of the wearing person and determines a fitting level on the basis of a reference pressure value (an atmospheric pressure value) and a mask inner pressure value measured by the mask inner pressure detection unit 2, and a display unit 3 that displays the fitting level determined by the circuit control unit to the wearing person as illustrated in FIGS. 1 to 3. In addition, the mask fitting level determination device according to the invention includes a battery unit (not illustrated) that supplies electric power to the circuit control unit and the display unit 3, a power supply switch 4 that starts and stops the supply of the electric power to these components, and a start switch 5 that starts a mask inner pressure detecting operation.

Further, the mask fitting level determination device according to the invention includes an opening/closing lid 7 provided at a main body 6, and as needed, the mask inner pressure detection unit 2 and an accommodation unit 8 for a cable C, which will be described later, are provided at the main body 6, and a mirror 9 for checking a wearing state of the mask 1 is provided inside the opening/closing lid 7. Since the mask inner pressure detection unit 2 is a precision electronic device, the mask inner pressure detection unit 2 is preferably accommodated in the accommodation unit 8 in order to prevent breakage and loss. The mirror 9 is preferably provided in order to actually view the wearing state of the mask 1.

The mask inner pressure detection unit 2 is connected to the main body 6 with the cable C and is inserted between the face surface F of the wearing person and the worn mask 1 via a flexible substrate B. The thickness of the flexible substrate B is equal to or less than 600 μm. The mask inner pressure detection unit 2 is provided with a pinchable clamp at an edge of the mask 1 although not illustrated in the drawing. The clamp is for preventing the mask inner pressure detection unit 2 from unexpectedly moving inside the mask 1, allows for accurate measurement of the mask inner pressure value, and prevents the wearing person from having an unpleasant feeling.

The mask inner pressure detection unit 2 is an ultra-small pressure sensor with a size in a level of several mm of a piezoresistive type and is preferably water-proofing. The mask inner pressure detection unit 2 does not become an obstacle inside the mask 1 by employing such an ultra-small pressure sensor and can be used even if a highly humid environment is achieved in the mask 1 by employing water-proofing.

Further, the mask inner pressure detection unit 2 can be provide with a wireless transmission function for transmitting information regarding the measured pressure value to the circuit control unit, and the circuit control unit can be provided with a wireless receiving function for receiving the information regarding the pressure value transmitted from the mask inner pressure detection unit 2. Mask fitting levels of a plurality of operators can be collectively managed by wirelessly connecting the mask inner pressure detection unit 2 to the circuit control unit in this manner, constantly measuring a difference in variation of a mask inner pressure, and transmitting the difference to an external device. The necessity of the cable C is eliminated by wirelessly connecting the mask inner pressure detection unit 2 to the circuit control unit in this manner, and the mask inner pressure detection unit 2 is more easily inserted between the face surface F of the wearing person and the mask 1.

The circuit control unit includes an internal information device such as a microcomputer attached thereto and is provide with a terminal (not illustrated) that can be connected to an external information device such as a personal computer or a smartphone such that programs of the microcomputer can be corrected and accumulated measurement history data and the like are retrieved, and electric power is supplied thereto from a battery unit (not illustrated) such as a battery incorporated in the main body 6. A difference in variation of a mask inner pressure caused by breathing of the wearing person can be recorded by connecting the circuit control unit to the personal computer. Also, a mask fitting level can be determined by a dedicated application by connecting the mask inner pressure detection unit 2 to a smartphone or a tablet.

For the measurement of the reference pressure value in the mask fitting level determination device according to the invention, the mask inner pressure detection unit 2 is taken out of the mask, and the atmospheric pressure at a location where the person wears the mask is measured again every several minutes. This is for obtaining an optimal reference pressure value when the mask fitting level is determined because there is a difference in variation of about 10 hPa at maximum in atmospheric pressure in a day and there is variation of several hPa in one hour.

The prescribed threshold value is set on the basis of a difference in variation between a mask inner pressure value caused by strength of breathing performed a plurality of times by the mask wearing person before the fitting level is determined and the reference pressure value. The mask inner pressure value at this time can be an average value of differences in variation of mask inner pressures caused by breathing performed a plurality of times or can be an n-th highest value of the differences in variation of mask inner pressures caused by breathing performed a plurality of times. The breathing of the wearing person is performed at a constant rhythm in accordance with LED display, buzzer sound, or the like of the start switch 5. The difference in variation of the mask inner pressure can be displayed on the display unit 3 in a stepwise manner in real time in accordance with the breathing of the wearing person.

The fitting level is determined on the basis of a difference in variation between the mask inner pressure value caused by strength of breathing performed a plurality of times by the mask wearing person when the fitting level is determined and the prescribed threshold value. The mask inner pressure value at this time can also be an average value of differences in variation of mask inner pressures caused by breathing performed a plurality of times or can be an n-th highest value of the differences in variation of mask inner pressures caused by breathing performed a plurality of times. The breathing of the wearing person is also performed at a constant rhythm in accordance with LED display, buzzer sound, or the like of the start switch 5 similarly to the case in which the prescribed threshold value is set. The difference in variation of the mask inner pressure can also be displayed on the display unit 3 in a stepwise manner in real time in accordance with breathing of the wearing person.

The display unit 3 is adapted to display the setting of the prescribed threshold value and the determination of the fitting level in a stepwise manner and includes a plurality of LEDs G1 to G3, for example, where G1 is a red LED, G2 is a yellow LED, and G3 is a green LED. The red LED G1 is turned on if the difference in variation between the mask inner pressure value caused by strength of breathing performed a plurality of times by the mask wearing person when the prescribed threshold value is set or when the fitting level is determined and the reference pressure value is equal to or greater than 0.4 hPa, for example, the yellow LED G2 is turned on if the difference is equal to or greater than 0.7 hPa, the green LED G3 is turned on if the difference is equal to or greater than 1.0 hPa, and the green LED G3 blinks if the difference is equal to or greater than 1.5 hPa. The wearing person can recognize the mask fitting level when the prescribed threshold value is set or when the fitting level is determined at a sight by the display unit 3 performing display in the stepwise manner in this manner.

Thus, the mask fitting level of the mask wearing person is determined using the mask fitting level determination device according to the invention in accordance with the following procedure.

First, the opening/closing lid 7 is opened as illustrated in FIG. 2 from the state illustrated in FIG. 1, and the mask inner pressure detection unit 2 and the cable C are taken out of the accommodation unit 8 of the main body 6.

Next, an operation of turning on the power supply switch 4 is performed in a state in which the cable C taken out is connected to the main body 6, the start switch 5 is pressed, and a reference pressure value (atmospheric pressure value) at a location where the person wears the mask is measured by the mask inner pressure detection unit 2. Thereafter, the mask 1 is attached to the face surface F, and the wearing person checks and adjusts how the mask 1 is attached while viewing the mirror 9 (it is not necessary to connect the cable C to the main body 6 in a case in which the mask inner pressure detection unit 2 and the circuit control unit are wirelessly connected). Then, the mask inner pressure detection unit 2 is inserted between the face surface F and the mask 1 (illustrated in FIG. 3), and as needed, the mask inner pressure detection unit 2 is pinched with a clamp at the edge of the mask 1. In a case in which the mask fitting level is immediately determined, the reference pressure value may be performed once. However, in a case in which it takes time to start the determination, the mask inner pressure detection unit 2 is taken out of the mask 1, and the reference pressure value (atmospheric pressure value) is measured again every several minutes.

Figure 5:
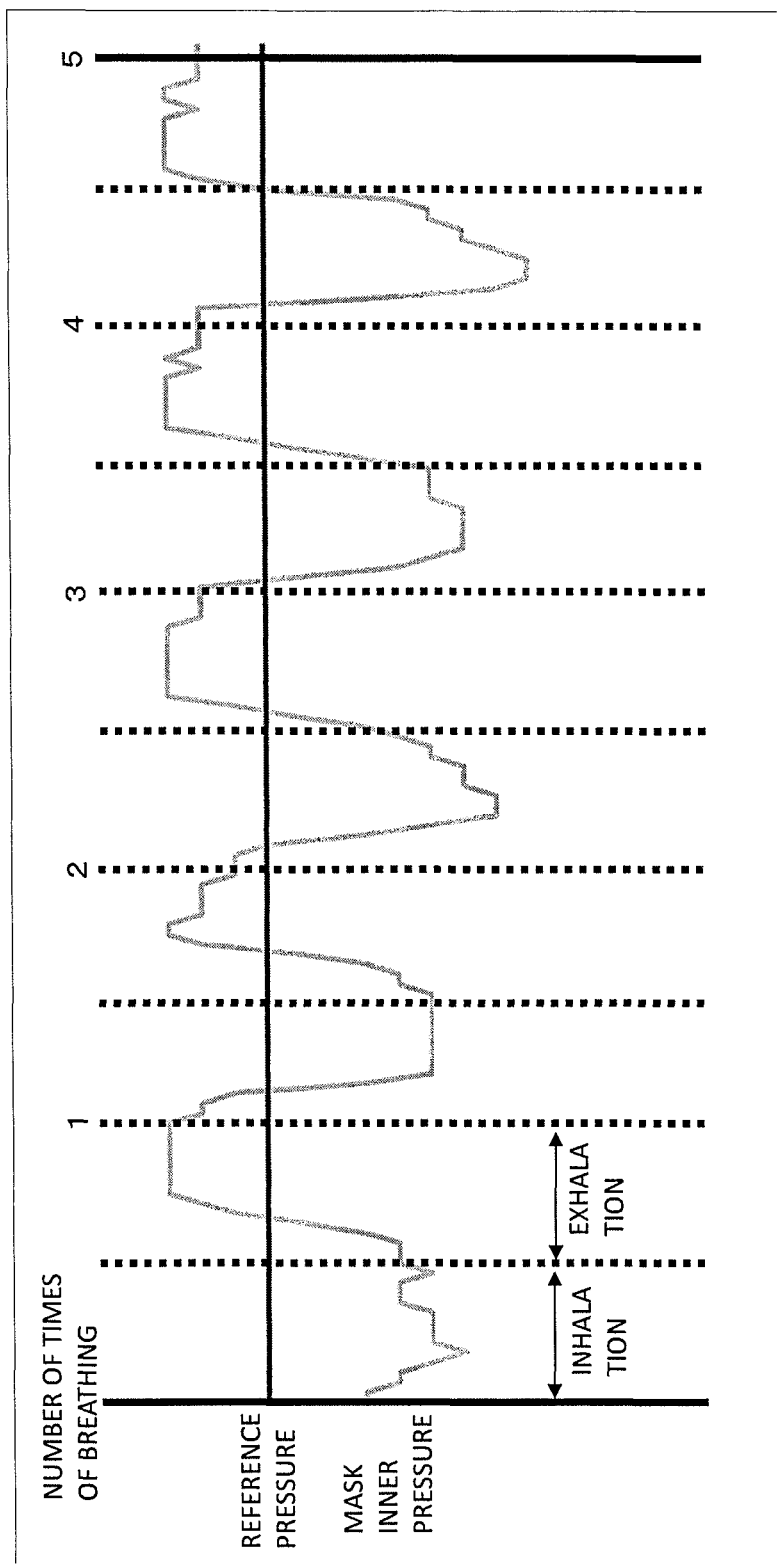
FIG. 5 is a graph illustrating a variation in mask inner pressure value when the mask fitting level determination device according to the invention sets a prescribed threshold value.

Thus, if the mask wearing person performs breathing a plurality of times (five times, for example) before the mask fitting level is determined, the mask inner pressure detection unit 2 measures mask inner pressure values. Since the measured mask inner pressure values vary as illustrated in FIG. 5 every time the breathing is performed, an average value thereof is obtained. Then, the circuit control unit sets a prescribe threshold value on the basis of a difference in variation between the average value of the mask inner pressure values and the reference pressure value.

The mask wearing person who sets the prescribe threshold value checks the mask fitting level when the prescribed threshold value is set through turning-on of the LEDs of the display unit 3. The fitting level is displayed in a stepwise manner by the display unit 3. For example, if G1 (red) or higher (equal to or greater than 0.4 hPa) is displayed through the turning-on of the LEDs of the display unit 3, it is determined that the threshold value can be set in the fitting level determination. In a case in which any of the LEDs of the display unit 3 is not turned on, the wearing person checks and adjusts how the mask 1 is attached, and similar setting operations are repeated again until the turning-on of the LEDs of the display unit 3 reaches G1 (red) or higher.

If the prescribed threshold value is stored in advance in the internal information device of the circuit control unit, it is not necessary to set the prescribed threshold value every time the mask is worn, and it is only necessary to perform the setting for the same user. Such a user can determine the mask fitting level without setting the prescribed threshold value from next time.

After the prescribe threshold value is set, the mask wearing person determines a mask fitting level. The mask inner pressure detection unit 2 measures mask inner pressure values if the wearing person performs breathing a plurality of times (five times, for example) even when the mask fitting level is determined. Since the measured mask inner pressure values also vary every time the breathing is performed similar to the case before the mask fitting level is determined, an average value thereof is obtained. Then, the circuit control unit determines the fitting level on the basis of a difference in variation between the average value of the mask inner pressure values and the prescribed threshold value.

The mask wearing person who determines the mask fitting level checks the mask fitting level through turning-on of the LEDs of the display unit 3. The fitting level is also displayed in a stepwise manner by the display unit 3. If G3 (green) is turned on among the LEDs of the display unit 3, for example, then it is determined that the mask fitting level is satisfactory. In a case in which G1 (red) or G2 (yellow) is turned on among the LEDs of the display unit 3, the wearing person checks and adjusts how the mask 1 is attached and similar determination operations are repeated again until G3 (green) is turned on among the LEDs of the display unit 3.

The mask fitting level determination device according to the invention configured as described above has a significantly simple component configuration, can be driven by a battery, can be reduced in size to a palm size, is inexpensive, is operated by a simple operation method, and does not require proficiency for accurate measurement as described above.

REFERENCE SIGNS LIST

1 Mask
2 Mask inner pressure detection unit
3 Display unit
F Face surface
B Flexible substrate

What is claimed is:

1. A mask fitting level determination device comprising:
   a mask inner pressure detection unit configured for insertion between a face surface of a wearing person and a worn mask;
   a circuit control unit configured to set a prescribed threshold value in accordance with strength of breathing of the wearing person and configured to determine a fitting level on the basis of a reference pressure measured by the mask inner pressure detection unit value and a mask inner pressure value measured by the mask inner pressure detection unit;
   a display unit configured to display the fitting level determined by the circuit control unit to the wearing person; and
   a flexible substrate, wherein the mask inner pressure detection unit is coupled to a portion of the flexible substrate, and wherein the portion of the flexible substrate with the mask inner pressure detection unit is positioned between the face surface of the wearing person and the worn mask.

2. The mask fitting level determination device according to claim 1, wherein the mask inner pressure detection unit is an ultra-small pressure sensor of a piezoresistive type.

3. The mask fitting level determination device according to claim 2, wherein for measurement of the reference pressure value, the mask inner pressure detection unit is removable from the mask, and an atmospheric pressure at a location where the person wears the mask is measurable again every several minutes.

4. The mask fitting level determination device according to claim 3, wherein the prescribed threshold value is configured to be set on the basis of a difference in variation between the mask inner pressure value and the reference pressure value.

5. The mask fitting level determination device according to claim 4, wherein the fitting level is configured to be determined on the basis of a difference in variation between a mask inner pressure value caused by strength of breathing performed a plurality of times by the mask wearing person when the fitting level is determined and the prescribed threshold value.

6. The mask fitting level determination device according to claim 1, wherein for measurement of the reference pressure value, the mask inner pressure detection unit is removable from the mask, and an atmospheric pressure at a location where the person wears the mask is measurable again every several minutes.

7. The mask fitting level determination device according to claim 1, wherein the mask inner pressure value caused by strength of breathing by the mask wearing person is performed a plurality of times is configured to be determined; and wherein the prescribed threshold value is configured to be set on the basis of a difference in variation between the mask inner pressure value and the reference pressure value.

8. The mask fitting level determination device according to claim 1, wherein the fitting level is configured to be determined on the basis of a difference in variation between a mask inner pressure-value caused by strength of breathing performed a plurality of times-by the mask wearing person when the fitting level is determined and the prescribed threshold value.

9. A mask fitting level determination method comprising:
inserting a mask inner pressure detection unit configured to be inserted between a face surface of a wearing person and a worn mask;
setting, using a circuit control unit, a prescribed threshold value in accordance with strength of breathing of the wearing person and determining a fitting level on the basis of a reference pressure value and a mask inner pressure value measured by the mask inner pressure detection unit; and
displaying the fitting level determined by the circuit control unit to the wearing person on a display unit;
wherein for measurement of the reference pressure value, the mask inner pressure detection unit is removed from the mask, and an atmospheric pressure at a location where the person wears the mask is measured again every several minutes.

10. The mask fitting level determination method according to claim 9, wherein the mask inner pressure detection unit is an ultra-small pressure sensor of a piezoresistive type and is inserted between the face surface of the wearing person and the worn mask via a flexible substrate.

11. The mask fitting level determination method according to claim 10, wherein for measurement of the reference pressure value, the mask inner pressure detection unit is removed from the mask, and an atmospheric pressure at a location where the person wears the mask is measured again every several minutes.

12. The mask fitting level determination device according to claim 11, wherein the prescribed threshold value is configured to be set on the basis of a difference in variation between the mask inner pressure value and the reference pressure value.

13. The mask fitting level determination device according to claim 12, wherein the fitting level is determined on the basis of a difference in variation between a mask inner pressure value caused by strength of breathing performed a plurality of times by the mask wearing person when the fitting level is determined and the prescribed threshold value.

14. The mask fitting level determination method according to claim 9, wherein the prescribed threshold value is set on the basis of a difference in variation between the mask inner pressure value and the reference pressure value.

15. The mask fitting level determination method according to claim 9, wherein the fitting level is determined on the basis of a difference in variation between a mask inner pressure value caused by strength of breathing performed a plurality of times by the mask wearing person when the fitting level is determined and the prescribed threshold value.

* * * * *